United States Patent [19]

Belkind

[11] 4,289,524
[45] Sep. 15, 1981

[54] HERBICIDAL 3-(TETRAHYDROBENZOTHIAZOL-2-YL)TETRAHYDRO-1,3,5-OXADIAZIN-4-ONES

[75] Inventor: Benjamin A. Belkind, Skokie, Ill.

[73] Assignee: Velsicol Chemical Coporation, Chicago, Ill.

[21] Appl. No.: 80,883

[22] Filed: Oct. 1, 1979

[51] Int. Cl.³ .................... A01N 43/78; C07D 273/04
[52] U.S. Cl. .................................. 71/90; 544/67
[58] Field of Search ............................ 71/90; 544/67

[56] References Cited

U.S. PATENT DOCUMENTS 3,655,659 4/1972 Driscoll .......................... 260/244R
3,696,101 5/1970 Litt et al. ...................... 260/248 NS

FOREIGN PATENT DOCUMENTS 1093407 3/1965 United Kingdom.

Primary Examiner—Catherine L. Mills
Attorney, Agent, or Firm—Dietmar H. Olesch; Robert J. Schwarz

[57] ABSTRACT

Disclosed are new compounds of the formula

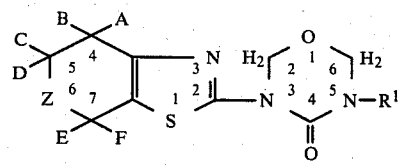

Wherein $R^1$ is selected from the group consisting hydrogen and alkyl; Z is selected from the group consisting of $-CHR^2-$, oxygen, sulfur and $-NR^3-$; $R^2$ and $R^3$ are selected from the group consisting of hydrogen and alkyl; A, C, and E are each independently selected from the group consisting of C1–C10 alkyl and hydrogen; B, D and F are each independently selected from the group consisting of C1–C10 alkyl, C3–C10 alkenyl, C4–C10 alkynyl, cycloalkyl, alkoxy, alkylthio, amino, cyano and hydrogen.

These compounds are useful as herbicides.

9 Claims, No Drawings

HERBICIDAL 3-(TETRAHYDROBENZOTHIAZOL-2-YL)TETRAHYDRO-1,3,5-OXADIAZIN-4-ONES

This invention relates to new compositions of matter and more specifically relates to new chemical compounds of the formula.

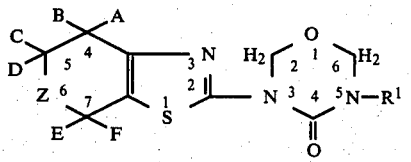
(I)

Wherein $R^1$ is selected from the group consisting of hydrogen and alkyl; Z is selected from the group consisting of —$CHR^2$—, oxygen, sulfur and —$NR^3$—; $R^2$ and $R^3$ are selected from the group consisting of hydrogen and alkyl; A,C and E are each independently selected from the group consisting of C1–C10 alkyl and hydrogen; B, D and F are each independently selected from the group consisting of C1–C10 alkyl, C3–C10 alkenyl, C4–C10 alkynyl, cycloalkyl, alkoxy, alkylthio, amino, cyano, and hydrogen.

The compounds of the present invention are useful as herbicides.

In a preferred embodiment of this invention, $R^1$ is selected from the group consisting of hydrogen and lower alkyl; Z is selected from the group consisting of —$CHR^2$—, oxygen, sulfur and —$NR^3$—; $R^2$ and $R^3$ are selected from the group consisting of hydrogen and lower alkyl; A,C, and E are each independently selected from the group consisting of lower alkyl and hydrogen; B,D, and F are each independently selected from the group consisting of lower alkyl, C3–C10 alkenyl, C4–C10 alkynyl, lower cycloalkyl, lower alkoxy, lower alkylthio, amino, cyano and hydrogen.

The term "lower" as used herein designates a straight or branched carbon chain of up to six carbon atoms or a cycloalkyl containing up to six carbon atoms.

The compounds of the present invention can be prepared by reacting a compound of formula.

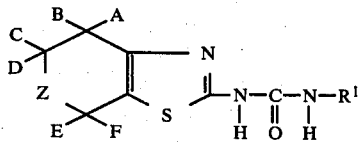
(II)

Wherein A,B,C,D,E,F,Z, and $R^1$ are as hereinbefore described, with s-trioxane. This reaction can be effected by adding approximately equimolar amounts of the compound of formula II and trioxane to cold sulfuric acid solution. After a suitable reaction period, the mixture is neutralized with a sodium hydroxide solution and the product isolated and purified by conventional techniques.

The compounds of formula II wherein $R^1$ is alkyl can be prepared by reacting a compound of formula.

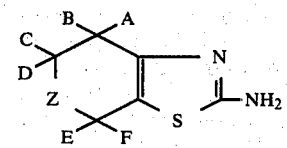
(III)

Wherein A,B,C,D,E,F and Z, are as hereinbefore described, with a compound of formula $R^1$—NCO     (IV)

Wherein $R^1$ is as heretofore described. This reaction can be effected by controlled addition of the compound of formula IV to a solution of the amine of formula III dissolved in an inert solvent such as ethyl acetate. Approximately equimolar amounts of the reactants are used. The reaction is carried out at room temperature and the reaction mixture stirred from 2 to 4 hours after the end of the addition of compound (IV). The product is isolated and purified by conventional means.

The compound of formula II wherein A,B,C,D,E,F, and Z are as hereinbefore described and $R^1$ is hydrogen may be prepared by the reaction of the compound of formula III with sodium or potassium cyanate. The reaction may be effected by combining approximately equimolar amounts of the cyanate and the amine in an acidic reaction medium. Acetic acid may be used and serves also as a solvent for the reactants. The reaction is carried out at about room temperature. The reaction mixture may be stirred from 0.25 to 2 hours after the initial mixing of reactants. Water may then be added to dissolved unreacted salt and the product then isolated and purified by art-known methods.

The compound of formula III may be prepared by reaction of a compound of formula.

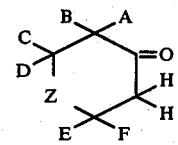
(V)

Wherein A,B,C,D,E,F, and Z are as heretofore described, with cyanamide and sulfur in the presence of a secondary amine. The reaction may be effected by slurrying approximately equimolar amounts of the cyclic ketone, cyanamide and sulfur in a non-reactive reaction medium such as ethanol, then slowly adding approximately an equimolar amount of a secondary amine such as diethylamine. The reaction mixture is preferably blanketed with an inert gas such as nitrogen and the reaction temperature is held to no higher than about 45° C. during the amine addition. At the conclusion of the amine addition, the reaction mixture is stirred for an additional 0.5 to 4 hours at a temperature of from about 40° to 45° C. It may then be added to an excess of water and acidified, with, for example, hydrochloric acid, and the unreacted organic reactants extracted. The aqueous solution of the product in the salt from is then made basic and the desired amine isolated and purified by conventional methods.

The compounds of formula III may also be made by various alternate routes such as are described in U.S. Pat. No. 3,682,945 issued Aug. 8, 1972 to Esso Research and Engineering Company.

Exemplary compounds of formula V suitable for preparing the compounds of the present invention are cyclohexanone; 3,5-dimethylcyclohexanone; 3-ethenylcyclohexanone; 4-(propynyl)cyclohexanone; 3-(cyclopentyl)cyclohexanone; 3,4-dimethoxycyclohexanone; 4-(ethylthio)cyclohexanone; 3-aminocyclohexanone; 4-aminocyclohexanone; 4-azacyclohexanone; 3-ethenyl-4-azacyclohexanone; 5-(3-butynyl)-4-azacyclohexanone; 3,3-dimethyl-4-azacyclohexanone; 3-cyclohexyl-4-azacyclohexanone; 3-ethylthio-4-azacyclohexanone; 1,3-dimethoxy-4-azacyclohexanone; 3-amino-4-azacyclohexanone; 4-thiacyclohexanone; 3,3-dimethyl-4-thiacyclo-hexanone; 3-(2-butenyl)-4-thiacyclohexanone; 3-(2-propynyl)-4-thiacyclohexanone; 3-(2,2-dimethylpropylthio)-4-thiacyclohexanone; 3-ethoxy-4-thiacyclohexanone; 3-amino-4-thiacyclohexanone; 6-cyclopentyl-4-thiacyclohexanone; 4-oxacyclohexanone; 3,3,5-trimethyl-4-oxacyclohexanone; 3-(3-pentenyl)-4-oxacyclohexanone; 3-(4-methyl-3-pentynyl)-4-oxacyclohexanone; 5-propoxy-4-oxacyclohexanone; 5-pentylthio-4-oxacyclohexanone; 3-cyclopropyl-4-oxacyclohexanone; 5-amino-4-oxacyclohexanone; and the like.

Exemplary compounds of formula IV suitable for preparing the compounds of the present invention are ethyl isocyanate, pentyl isocyanate, 2-ethylbutyl isocyanate and the like.

The manner in which the compounds of the present invention can be prepared is more specifically illustrated in the following examples.

EXAMPLE 1

Preparation of 2-AMINO-5,5,7,7-TETRAMETHYL-4,5,6,7-TETRAHYDROBENZOTHIAZOLE 3,3,5,5-Tetramethylcyclohexanone (49.5 grams; 0.32 mole), cyanamide (10.5 grams; 0.25 mole). sulfur (8.0 grams 0.25 mole) and ethanol (40 ml) were charged into a glass reaction vessel fitted with a mechanical stirrer, thermometer and reflux condenser. The mixture was blanketed with nitrogen and diethylamine (25 ml) was added dropwise, with stirring, over a 30 minute period. The reaction was exothermic, external cooling was applied to hold the temperature of the reaction mixture no higher than 45° C. At the conclusion of the amine addition, the reaction mixture was stirred for a period of about 2 hours while using external heat to keep the temperature at about 40°-45° C. The reaction mixture was then poured into water (100 ml) and acidified with concentrated hydrochloric acid to a pH of 4. The unreacted ketone was extracted with six 25 ml washes of diethyl ether, the aqueous portion was then taken to pH 9 by addition of 50% aq. sodium hydroxide and extracted with diethyl ether. The ether extracts were combined, dried over magnesium sulfate, filtered and the solvent removed on a rotary evaporator to yield the desired product 2-amino-5,5,7,7-tetramethyl4,5,6,7-tetrahydrobenzothiazole as a solid with a melting point of 120°-122° C.

EXAMPLE 2

Preparation of N-(5,5,7,7-TETRAMETHYL-4,5,6,7-TETRAHYDROBENZOTHIAZOL-2-YL)-N'-METHYLUREA 2-Amino-5,5,7,7-tetramethyl-4,5,6,7-tetrahydrobenzothiazole (21 grams; 0.1 mole) was dissolved in ethyl acetate (100 ml) and the solution charged into a glass reaction vessel fitted with a mechanical stirrer and thermometer. Methyl isocyanate (6.2 grams 0.11 mole) was added dropwise to this solution over a period of 30 minutes. The temperature of the reactants was at about 20°-25° C. during the addition. At the conclusion of the isocyanate addition, stirring was continued at room temperature for a period of about 2 hours. The desired product, 2-amino-5,5,7,7-tetramethyl-4,5,6,7-tetrahydrobenzothiazole, a solid, was then filtered from the reaction mixture and air dried. Its melting point was greater than 250° C.

EXAMPLE 3

Preparation of 3-(5,5,7,7-TETRAMETHYL-4,5,6,7-TETRAHYDROBENZOTHIAZOL-2YL)-5-METHYLTETRAHYDRO-1,3,5-OXADIAZIN-4-ONE

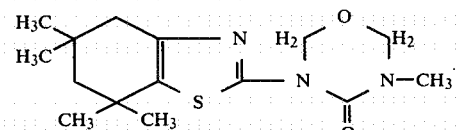

Sulfuric acid, 85% concentration (40 grams) was charged into a glass reaction vessel fitted with a mechanical stirrer and a thermometer and was cooled to about 5° C. N-(5,5,7,7-tetramethyl-4,5,6,7-tetrahydrobenzothiazol-2-yl)-N'-methylurea (4.1 grams; 0.015 mole) and s-trioxane (1.4 grams, 0.015 mole) were added portionwise, with stirring, to the cold sulfuric acid. Stirring was continued for a period of about 16 hours at a temperature of about 20°-25° C. The reaction mixture was then diluted 1:1 with water and neutralized with aqueous 40% sodium hydroxide. The neutralized mixture was filtered and the solid obtained was washed with 3-100 ml portions of water and air dried to yield the desired product 3-(5,5,7,7-tetramethyl-4,5,6,7-tetrahydro-benzothiazol-2-yl)-5methyltetrahydro-1,3,5-oxadiazin-4-one as a solid having a melting point of 138°-140° C. Elemental analysis: Theory: C: 58.22%; H: 7.49%; N: 13.58%; Found: C:57.53%; H: 7.57%; N: 13.61%.

EXAMPLE 4

Preparation of N-(5,5,7,7-TETRAMETHYL-4,5,6,7-TETRAHYDROBENOTHIAZOL-2-YL)-N'-HEXYLUREA 2-Amino-5,5,7,7-tetramethyl-4,5,6,7-tetrahydrobenzothiazole (0.1 mole) is dissolved in ethyl acetate (100 ml) and the solution is charged into a glass reaction vessel fitted with a stirrer and thermometer. Hexyl isocyanate (0.11 mole) is added dropwise to this solution over a period of about 30 minutes. The temperature of the reactants is at about 20° to 25° C. during the addition. At the end of the addition stirring is continued at room temperature for a period of about 2 hours. The reaction mixture is then filtered and the filtered-off solids air dried to yield the desired product N-(5,5,7,7-tetramethyl-4,5,6,7-tetrahydrobenthiazol-2-yl)-N-hexylurea.

EXAMPLE 5

Preparation of
3-(5,5,7,7-TETRAMETHYL-4,5,6,7-TETRAHYDROBENZOTHIAZOL-2-YL)-5-HEXYLTETRAHYDRO-1,3,5-OXADIAZIN-4-ONE

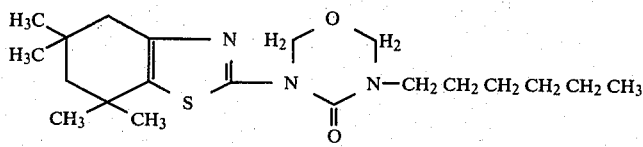

Sulfuric acid, 85% concentration, (40 grams) is charged into a glass reaction vessel fitted with a mechanical stirrer and thermometer and is cooled to about 5° C. N-(5,5,7,7-tetramethyl-4,5,6,7-tetrahydrobenzothiazol-2-yl)-N'-hexylurea (0.015 mole) and s-trioxane (0.015 mole) are added portionwise, with stirring to the cold sulfuric acid. Stirring is continued for a period of about 16 hours at room temperature. The reaction mixture is then diluted 1:1 with water and neutralized with aqueous 40% sodium hydroxide. The neutralized mixture is filtered and the filtered-off solid is washed with 3–100 ml portions of water and air dried to yield the desired product 3-(5,5,7,7-tetramethyl-4,5,6,7-tetrahydrobenzothiazol-2-yl)-5-hexyltetrahydro-1,3,5-oxadiazin-4-one.

EXAMPLE 6

Preparation of
N-(5,5,7,7-TETRAMETHYL-4,5,6,7-TETRAHYDROBENZOTHIAZOL-2-YL)UREA

2-Amino-5,5,7,7-tetramethyl-4,5,6,7-tetrahydrobenzothiazole (0.3mole), potassium cyanate (0.3 mole) and concentrated acetic acid (90 ml) are charged into a glass reaction vessel fitted with a mechanical stirrer and thermometer. A mild exotherm is noted at the beginning of the reaction. Stirring is continued for a period of about 1 hour with no external heating. Water (90 ml) is added and the resulting mixture filtered. The filtered-off solids are recrystallized from methanol to yield the desired product N-(5,5,7,7-tetramethyl-4-5,6,7-tetrahydrobenzothiazol-2-yl)urea.

EXAMPLE 7

Preparation of
3-(5,5,7,7-TETRAMETHYL-4,5,6,7-TETRAHYDROBENZOTHIAZOL-2-YL)TETRAHYDRO-1,3,5-OXADIAZIN-4-ONE

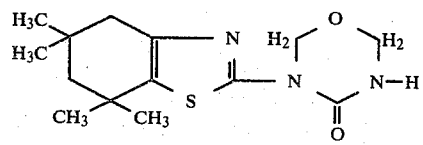

Sulfuric acid, 85% concentration, (40 grams) is charged into a glass reaction vessel fitted with a mechanical stirrer and thermometer and is cooled to about 5° C. 2-Amino-5,5,7,7-tetramethyl-4,5,6,7-tetrahydrobenzothiazole (0.015 mole) and s-trioxane (0.015 Mole) are added portionwise, with stirring, to the cold sulfuric acid. Stirring is continued for a period of about 16 hours at room temperature. The reaction mixture is then diluted 1:1 with water and neutralized with aqueous 40% sodium hydroxide. The neutralized mixture is filtered and the filtered-off solid is washed with 3–100 ml portions of water and air dried to yield the desired product 3-(5,5,7,7-tetramethyl-4,5,6,7-tetrahydrobenzothiazol-2-yl)tetrahydro-1,3,5-oxadiazine-4-one.

EXAMPLE 8

Preparation of
2-AMINO-5,5,7-TRIMETHYL-4,5,6,7-TETRAHYDROBENZOTHIAZOLE

Dihydroisophorone (0.3 mole), cyanamide (0.25 mole) sulfur (0.25 mole) and ethanol (40 ml) are charged into a glass reaction vessel fitted with a mechanical stirrer, thermometer and reflux condenser. The mixture is blanketed with nitrogen and diethylamine (25 ml) is added dropwise, with stirring, over a 30 minute period. The reaction temperature is kept no higher than 45° C. during the amine addition. At the conclusion of the amine addition, the reaction mixture is stirred for a period of about 2 hours while heating to keep the temperature at about 40° C. to 45° C. The reaction mixture is then poured into water (100 ml) and acidified to a pH of 4 with concentrated hydrochloric acid. The unreacted ketone is extracted with six 25 ml washes of diethyl ether; the aqueous portion is then taken to pH 9 by addition of 50% aqueous sodium hydroxide and is extracted with diethyl ether. The ether extracts are combined, dried over magnesium sulfate, filtered and the solvent removed on a rotary evaporator to yield the desired product 2-amino-5,5,7-trimethyl-4,5,6,7-tetrahydrobenzothiazole.

EXAMPLE 9

Preparation of
N-(5,5,7-TRIMETHYL-4,5,6,7-TETRAHYDROBENZOTHIAZOLE-2-yl)-N'-METHYLUREA 2-Amino-5,5,7-trimethyl-4,5,6,7-tetrahydrobenzothiazole (0.1 mole) is dissolved in ethyl acetate (100 ml) and the solution is charged into a glass reaction vessel fitted with a stirrer and thermometer. Methyl isocyanate (0.11 mole) is added dropwise to this solution over a period of about 30 minutes. The temperature of the reactant is held at about 20° C. to 30° C. during the addition. At the end of the addition, stirring is continued at room temperature for a period of about 2 hours. The reaction mixture is then filtered and the filtered-off solids are air dried to yield the desired product N-(5,5,7-trimethyl-4,5,6,7-tetrahydrobenzothiazol-2-yl)-N'-methylurea.

EXAMPLE 10

Preparation of
3-(5,5,7-TRIMETHYL-4,5,6,7-TETRAHYDROBEN-
ZOTHIAZOL-2-yl)-5-METHYLTETRAHYDRO-
1,3,5-OXADIAZIN-4-ONE

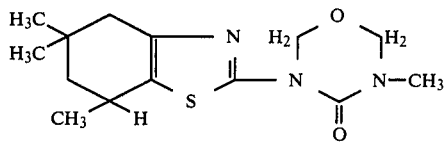

Sulfuric acid, 85% concentration, (40 grams) is charged into a glass reaction vessel fitted with a mechanical stirrer and thermometer and is cooled to about 5° C. N-(5,5,7-trimethyl-4,5,6,7-tetrahydrobenzothiazol-2-yl)-N'-methylthiourea (0.015 mole) and s-trioxane (0.015 mole) are added portionwise, with stirring to the cold surfuric acid. Stirring is continued for a period of about 16 hours at room temperature. The reaction mixture is then diluted 1:1 with water and neutralized with aqueous 40% sodium hydroxide. The neutralized mixture is filtered and the filtered-off solid is washed with 3–100 ml portions of water and air dried to yield the desired product 3-(5,5,7-trimethyl-4,5,6,7-tetrahydrobenzothizol-2-yl)-5-methyltetrahydro-1,3,5-oxidiazin-4-one.

EXAMPLE 11

Preparation of
2-AMINO-6-THIA-4,5,6,7-TETRAHYDROBENZO-
THIAZOLE

Thiacyclohexan-4-one (0.3 mole), cyanamide (0.25 mole), sulfur (0.25 mole) and ethanol (40 ml) are charged into a glass reaction vessel fitted with a mechanical stirrer, thermometer and reflux condenser. The mixture is blanketed with nitrogen and diethylamine (25 ml) is added dropwise, with stirring, over a 30 minute period. The reaction temperature is kept no higher than 45° C. during the amine addition. At the conclusion of the amine addition, the reaction mixture is stirred for a period of about 2 hours while heating to keep the temperature at about 40° C. to 45° C. The reaction mixture is then poured into water (100 ml) and acidified to a pH of 4 with concentrated hydrochloric acid. The unreacted ketone is extracted with six-25 ml washes of diethyl ether; the aqueous portion is then taken to pH 9 by addition of 50% aqueous sodium hydroxide and is extracted with diethyl ether. The ether extracts are combined, dried over magnesium sulfate, filtered and the solvent removed on a rotary evaporator to yield the desired product 2-amino-6-thia-4,5,6,7-tetrahydrobenzothiazole.

EXAMPLE 12

Preparation of
N-(6-THIA-4,5,6,7-TETRAHYDROBENZO-
THIAZOL-3-YL)-N-BUTYLUREA

2-Amino-6-thia-4,5,6,7-tetrahydrobenzothiazole (0.1 mole) is dissolved in ethyl acetate (100 ml) and the solution is charged into a glass reaction vessel fitted with a stirrer and thermometer. Butyl isocyanate (0.11 mole) is added dropwise to this solution over a period of about 30 minutes. The temperature of the reactants is at about 20° to 25° C. during the addition. At the end of the addition stirring is continued at room temperature for a period of about 2 hours. The reaction mixture is then filtered and the filtered-off solids air dried to yield the desired product N-(6-thia-4,5,6,7-tetrahydrobenzothiazol-2-yl)-N'-butylurea.

EXAMPLE 13

Preparation of
3-(6-THIA-4,5,6,7-TETRAHYDROBENZO-
THIAZOL-2-YL)-5-BUTYLTETRAHYDRO-1,3,5-
OXADIAZIN-4-ONE

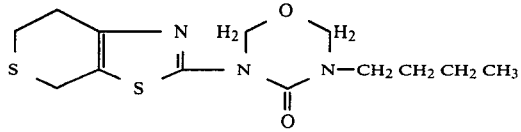

Sulfuric acid, 85% concentration, (40 grams) is charged into a glass reaction vessel fitted with a mechanical stirrer and thermometer and is cooled to about 5° C. N-(6-Thia-4,5,6,7-tetrahydrobenzothiazol-2-yl)-N'-butylurea (0.015 mole) and s-trioxane (0.015 mole) are added portionwise, with stirring, to the cold sulfuric acid. Stirring is continued for a period of about 16 hours at room temperature. The reaction mixture is then diluted 1:1 with water and neutralized with aqueous 40% sodium hydroxide. The neutralized mixture is filtered and the filtered-off solids are washed with 3–100 ml portions of water and air dried to yield the desired product 3-(6-thia-4,5,6,7-tetrahydrobenzothiazol-2-yl)-5-butyltetrahydro-1,3,5-oxadiazin-4-one.

EXAMPLE 14

Preparation of
2-AMINO-6-AZA-6-METHYL-4,5,6,7-TETRAHY-
DROBENZOTHIAZOLE

1-Methyl-4-piperidone (0.3 mole), cyanamide (0.25 mole), sulfur (0.25 mole) and ethanol (40 ml) are charged into a glass reaction vessel fitted with a mechanical stirrer, thermometer and reflux condenser. The mixture is blanketed with nitrogen and diethylamine (25 ml) is added dropwise, with stirring, over a 30 minute period. The reaction temperature is kept no higher than 45° C. during the amine addition. At the conclusion of the amine addition, the reaction mixture is stirred for a period of about 2 hours while heating to keep the temperature at about 40° C. to 45° C. The reaction mixture is then poured into water (100 ml) and acidified to a pH of 4 with concentrated hydrochloric acid. The unreacted ketone is extracted with six-25 ml washes of diethyl ether; the aqueous portion is then taken to pH 9 by addition of 50% aqueous sodium hydroxide and is extracted with diethyl ether. The ether extracts are combined, dried over magnesium sulfate, filtered and the solvent removed on a rotary evaporator to yield the desired product 2-amino-6-aza-6-methyl-4,5,6,7-tetrahydrobenzothiazole.

EXAMPLE 15

Preparation of
N-(6-AZA-6-METHYL-4,5,6,7-TETRAHY-
DROBENZOTHIAZOL-2-YL)-N'-ETHYLUREA 2-Amino-6-aza-6-methyl-4,5,6,7-tetrahydrobenzothiazole (0.1 mole) is dissolved in ethyl acetate (100 ml) and the solution is charged into a glass reaction vessel fitted with a stirrer and thermometer. Ethyl isocyanate (0.11 mole) is added dropwise to this solution over a period of about 30 minutes. The temperature of the reactants is at about 20° C. to 25° C. during the addition. At the end of the addition, stirring is continued at room temperature for a period of about 2 hours. The reaction mixture is then filtered and the filtered-off solids air dried to yield the desired product N-(6-aza-6-methyl-4,5,6,7-tetrahydrobenzothiazol-2-yl)-N-ethylurea.

EXAMPLE 16

Preparation of
3-(6-AZA-6-METHYL-4,5,6,7-TETRAHYDROBEN-ZOTHIAZOL-2-YL)-5-ETHYLTETRAHYDRO-1,3,5-OXADIAZIN-4-one

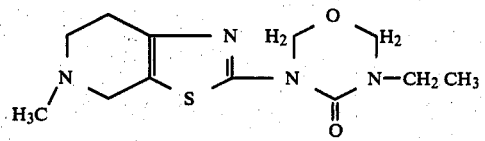

Sulfuric acid, 85% concentration, (40 grams) is charged into a glass reaction vessel fitted with a mechanical stirrer and a thermometer and is cooled to about 5° C. N-(6-aza-6-methyl-4,5,6,7-tetrahydrobenzothiazol-2-yl)N'-ethylurea (0.015 mole) and s-trioxane (0.015 mole) are added portionwise, with stirring, to the cold sulfuric acid. Stirring is continued for a period of about 16 hours at room temperature. The reaction mixture is then diluted 1:1 with water and neutralized with aqueous 40% sodium hydroxide. The neutralized mixture is filtered and the filtered-off solid is washed with 3-100 ml portions of water and air dried to yield the desired product 3-(6-aza-6-methyl-4,5,6,7-tetrahydrobenzothiazol-2-yl)-5-ethyltetrahydro-1,3,5-oxadiazin-4-one.

Additional compounds within the scope of the present invention which can be prepared according to the procedures detailed in the foregoing examples include: 3-[5,7-di(3-hexenyl)-4,5,6,7-tetrahydrobenzothiazol-2-yl]-5-methyltetrahydro-1,3,5-oxadiazin-4-one; 3-[4,5-di(4-hexynyl)-7-cyano-4,5,6,7-tetrahydrobenzothiazol-2-yl]-5-methyltetrahydro-1,3,5-oxadiazin-4-one; 3-(4,7-hexyloxy-5-ethylthio-4,5,6,7-tetrahydrobenzothiazol-2-yl)-5-methyltetrahydro-1,3,5-oxadiazin-4-one; 3-[4,5,7-tri(buthylthio)-4,5,6,7-tetrahydrobenzothiazol-2-yl]-5-methyltetrahydro-1,3,5-oxadiazin-4-one; 3(5,5,7-trimethyl-1-amino-4,5,6,7-tetrahydrobenzothiazol-2-yl)-5-methyltetrahydro-1,3,5-oxadiazin-4-one; 3-(4-cyclohexyl-5-ethyl-4,5,6,7-tetrahydrobenzothiazol-2-yl)-5-methyltetrahydro-1,3,5-oxadiazin-4-one; 3-(5,5-dipropyl-6-ethyl-7-cyano-4,5,6,7-tetrahydrobenzothiazol-2-yl)-5-methyltetrahydro-1,3,5-oxadiazin-4-one; 3-(4,5,6,7-tetramethyl-6-oxa4,5,6,7-tetrahydrobenzothiazol-2-yl)-5-methyltetrahydro-1,3,5-oxadiazin-4-one; 3-[5-(2-methyl-2-butenyl)-6-oxa-7,7-dimethyl4,5,6,7-tetrahydrobenzothiazol-2-yl]-5-methyltetrahydro-1,3,5-oxadiazin-4-one; 3-[4,4-dimethyl-5-(2,2-dimethyl-3-butynyl)-6-oxa-7-methyl-4,5,6,7-tetrahydrobenzothiazol-2-yl]-5-methyltetrahydro-1,3,5-oxadiazin-4-one; 3-(4,7-dicyano-5-ethyl-6-oxa-4,5,6,7-tetrahydrobenzothiazol-2-yl)-5-methyltetrahydro-1,3,5-oxadiazin-4-one; 3-(5-cyclopentyl-6-oxa-4,5,6,7-tetrahydrobenzothiazol-2-yl)-5-methyltetrahydro-1,3,5-oxadiazin-4-one; 3-(4,5,7-triethoxy-6-oxa-4,5,6,7-tetrahydrobenzothiazol-2-yl)-5-propyltetrahydro-1,3,5-oxadiazin-4-one; 3-[5,7-di(-butylthio)-6-oxa-4,5,6,7-tetrahydrobenzothiazol-2-yl]-5-propyltetrahydro-1,3,5-oxadiazin-4-one; 3-(4-amino-6-oxa-4,5,6,7-tetrahydrobenzothiazol-2-yl)-5-propyltetrahydro1,3,5-oxadiazin-4-one; 3-[4-methyl-5,7-di(2-pentenyl)-6-thia-4,5,6,7-tetrahydrobenzothiazol-2-yl]-5-methyltetrahydro-1,3,5-oxadiazin-4-one; 3-[5-(2-hexenyl)6-thia-7-cyano-4,5,6,7-tetrahydrobenzothiazol-2-yl]-5-methyltetrahydro-1,3,5l-oxadiazin-4-one; 3-(4-ethoxy-5-methyl-6-thia-4,5,6,7-tetrahydrobenzothiazol-2-yl)-5-methyltetrahydro-1,3,5-oxadiazin-4-one; 3-(4,4-dimethyl-5-cyano-6-thia-4,5,6,7-tetrahydrobenzothiazol-2-yl)-5-methyltetrahydro-1,3,5-oxadiazin-4-one; 3-[6-thia-7-(1,1-dimethylethylthio)-4,5,6,7-tetrahydrobenzothiazol-2-yl]-5-methyltetrahydro-1,3,5-oxadiazin-4-one; 3-(4,4,5-trimethyl-6-thia-7-cyclopentyl-4,5,6,7-tetrahydrobenzothiazol-2-yl)-5-methyltetrahydro-1,3,5-oxadiazin-4-one; 3-(4-amino-5,7-dimethyl-6-thia-4,5,6,7-tetrahydrobenzothiazol-2-yl)-5-methyltetrahydro-1,3,5-oxadiazin-4-one; 3-[3-pentenyl)-5,5-diethyl-6-aza-4,5,6,7-tetrahydrobenzothiazol-2-yl]-5-butyltetrahydro-1,3,5-oxadiazin-4-one; 3-(4-butoxy-5-hexyl-6-aza-7-cyano-4,5,6,7-tetrahydrobenzothiazo-2-yl)-5-butyltetrahydro-1,3,5-oxadiazin-4-one; 3-(amino-5,5-dimethyl-6-aza-7-cyclopentyl-4,5,6,7-tetrahydrobenzothiazol-2-yl)-5-butyltetrahydro-1,3,5-oxadiazin-4-one; 3-(4-butylthio-5-butyl-6-aza-4,5,6,7-tetrahydrobenzothiazol-2-yl)-5-butyltetrahydro-1,3,5-oxadiazin-4-one; 3-(4-ethyl-5-ethenyl-6-aza-6-ethyl-4,5,6,7-tetrahydrobenzothiazol-2-yl)-5-ethyltetrahydro-1,3,5-oxadiazin-4-one; 3-(4-cyclobutyl-5,5-dimethyl-6-aza-6-propyl-4,5,6,7-tetrahydrobenzothiazol-2-yl)-5-ethyltetrahydro-1,3,5-oxadiazin-4-one; 3-[4-(2-methyl-3-butynyl)-6-aza-6-butyl-4,5,6,7-tetrahydrobenzothiazol-2-yl]-5-ethyltetrahydro-1,3,5-oxadiazin-4-one; 3-[4-hexyloxy-6-aza-6-(2-methylpropyl)-4,5,6,7-tetrahydrobenzothiazol-2-yl]-5-ethyltetrahydro-1,3,5-oxadiazin-4-one; 3-(4-butylthio-6-aza-6l-methyl-7-ethyl-4,5,6,7-tetrahydrobenzothiazol-2-yl)-5-ethyltetrahydro-1,3,5-oxadiazin-4-one; 3-(4-cycano-6-aza-6-butyl-7,7-dimethyl-4,5,6,7-tetrahydrobenzothiazol-2-yl)-5-ethyltetrahydro-1,3,5-oxadiazin-4-one; 3-(4-amino-6-aza-6-ethyl-4,5,6,7-tetrahydrobenzothiazol-2-yl)-5-ethyltetrahydro-1,3,5-oxidiazin-4one and the like.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water of oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atomospheric pressure as aerosols. However, preferred liquid herbicidal compositions are emulsifiable concentrates which comprise an active compound according to this invention and as the inert carrier a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestions.

A typical herbicidal composition according to this invention is illustrated by the following example, in which the quantities are in parts by weight.

EXAMPLE 17

Preparation of a Dust

Product of Example 3: 10
Powdered Talc: 90

The above ingredients are mixed in a mechanical grinderblender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors and the like in the herbicidal compositions heretofore described. These other materials can comprise from about 5% to about 95% of the active ingredients in the herbicidal compositions. Use of combinations these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and the plant growth inhibitors, with which the compounds of this invention can be used in the herbicical compositions to control weeds, can include chlorophenoxy herbicides such as 2,4-D, 2,4,5-T, MCPA, MCPB, 4(2,4-DB,) 2,4,-DEB, 4-CPB, 4-CPA, 4-CPP, 2,4,5-TES, 3,4-DA, silvex and the like; carbamate herbicides such as IPC, CIPC, swep barban, BCPC, CEPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, momolinuron, neburon, buturon, trimeturon and the like; symmetrical triazine herbicides such as simazine, chlorazine, atraone, desmetryne, norazine, ipazine, prometryn, atrazine, trietazine, simetone, prometone, propazine, ametryne, and the like; chloracetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine, 1-(chloroacetyl)-piperidine and the like; chlorinated aliphatic acid herbicides such as TCA, dalapon, 2,3-dichloropionic acid, 2,2,3-TPA and the like; chlorinated benzoic acid and phenyl-acetic herbicides such as 2,3,6-TBA, 2,3,5,6-TBA, dicamba, tricamba, amiben, fenac, PBA, 2-methyoxy-3-, 6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephtalate, diquat, erbon, DNC, DNBP, dichlobenil, CPA, diphenamid, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine, 3,5-dione, bromoxynil, cacodylic acid, CMA, CPMF, cypromid, DCB, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, wild buckwheat, kochia, medic, corn cockle, ragweed, sowthistle, coffeeweed, croton, cuphea, dodder, fumitory, groundsel, hemp nettle, knawel, spurge, spurry, emex, jungle rice, pondweed, dog fennel, carpetweed, morningglory, bedstraw, duchsalad, naiad, cheatgrass, fall panicum, jimsonweed, witchgrass, switchgrass, watergrass, teaweed, wild turnip and sprangletop; biennials such as wild carrot, matricaria, wild barley, campion, chamomile, burdock, mullein, roundleaved mallow, bull thistle, hounds-tongue, moth mulein and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail and wintercress, horsenettle, nutsedge, milkweed and sicklepod.

Similarly, such weeds can be classified as broadleaf or grassy weeds. It is economically desirable to control the growth of such weeds without damaging beneficial plants of livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention can be demonstrated by experiments carried out for the pre-emergence control of a variety of weeds. In these experiments small plastic greenhouse pots filled with dry soil are seeded with the various weed seeds. Twenty-four hours or less after seeding the pots are sprayed with water until the soil is wet and the test compound dissolved in a solvent comprising a mixture of 45 volumes acetone, 2 volumes methanol and one volume N,N-dimethylformamide is sprayed at the indicated concentrations of the surface of the soil.

After spraying, the soil containers are placed in the greenhouse and provided with supplementary heat as required and daily or more frequent watering. The plants are maintained under these conditions for a period of from 15 to 21 days, at which time the condition of the plants and the degree of injury to the plants is rated on a scale of from 0 to 10, as follows: 0=no injury, 1,2=slight injury, 3,4=moderate injury, 5,6=moderately severe injury, 7,8,9=severe injury, 10=death and N.E.=No emergence of the plant. The effectiveness of these compounds is demonstrated by the data in Table 1 below.

The herbicidal activity of the compounds of this invention can also be demonstrated by experiments carried out for the post-emergence control of a variety of weeds. In these experiments the compounds to be tested are formulated as aqueous emulsions and sprayed at the desired dosage on the foliage of the weeds that have attained a prescribed size. After spraying the plants are placed in a greenhouse and watered daily or more frequently. Water is not applied to the foliage of the treated plants. The severity of the injury is determined 14 days after treatment and is rated on the scale of from 0 to 10 heretofore described. The effectiveness of these compounds is demonstrated by the data in Table 2 below.

The abbreviations used for plant species in the tables are:

| Plant Species | Abbreviation |
| --- | --- |
| Yellow Nutsedge | YNSG |
| Wild Oats | WOAT |
| Jimsonweed | JMWD |
| Velvetleaf | VTLF |
| Johnsongrass | JNGS |
| Pigweed | PIGW |
| Wildmustard | WMSTD |
| Yellow Foxtail | YFLX |
| Barnyardgrass | BNGS |
| Crabgrass | CBGS |
| Cheatgrass | CTGS |
| Wild Morningglory | MNGY |
| Bindweed | BDWD |
| Soybean | SOYB |
| Sugar Beet | SUBT |
| Sorghum | SORG |
| Wheat | WHT |
| Rice | RICE |
| Cotton | COTN |
| Quackgrass | QKGS |
| Corn | CORN |
| Pinto Bean | PTBN |
| Alfalfa | ALFA |
| Cheatgrass | CTGS |
| Oat | OAT |
| Sprangletop | SPGT |

TABLE 1

| COMPOUND OF EXAMPLE 3: | INJURY RATINGS Plant Species | | | | | | | | | | | |
| --- | --- | --- | --- | --- | --- | --- | --- | --- | --- | --- | --- | --- |
| | WMSTD | YLFX | BNGS | CBGS | CTGS | MNGY | YNSG | WOAT | JMWD | VTLF | JNGS | PIGW |
| 14 days after treatment | | | | | | | | | | | | |
| 8 lbs./acre application rate | 10 | 5 | 7 | 8 | 10 | 10 | N.E. | 10 | 9 | 10 | 2 | 9 |
| 2 lbs./acre application rate | 10 | 2 | 3 | 7 | 3 | 4 | 0 | 3 | 3 | 9 | 0 | 4 |
| 1 lbs./acre application rate | 10 | 0 | 0 | 3 | 0 | 0 | 0 | 1 | 2 | 8 | 0 | 4 |
| 21 days after treatment | | | | | | | | | | | | |
| 8 lbs/acre application rate | 10 | 2 | 8 | 9 | 10 | 10 | 4 | 10 | 9 | 10 | 3 | 0 |
| 2 lbs/acre application rate | 10 | 0 | 2 | 2 | 3 | 1 | 0 | 1 | 4 | 9 | 1 | 0 |
| 1 lbs/acre application rate | 10 | 0 | 2 | 1 | 0 | 1 | 0 | 0 | 2 | 4 | 0 | 0 |

TABLE 2
INJURY RATINGS

COMPOUND OF EXAMPLE 3:

| | | Plant Species | | | | | |
|---|---|---|---|---|---|---|---|
| | | YFLX | JNGS | MNGY | JMWD | YNSG | PIGW |
| 14 | days after treatment | | | | | | |
| 8 | lbs/acre application rate | 9 | 8 | 10 | 10 | 0 | 10 |
| 2 | " | 5 | 6 | 10 | 10 | 0 | 10 |
| 1 | " | 3* | 2* | 10* | 10* | 0 | 8* |
| 0.5 | " | 0 | 0 | 4 | 10 | — | 6 |
| 0.25 | " | 0 | 0 | 4 | 4 | — | 6 |
| 0.125 | " | 0 | 0 | 1 | 3 | — | 6 |

| | | Plant Species | | | | | |
|---|---|---|---|---|---|---|---|
| | | WMSTD | WOAT | BDWD | BNGS | SOYB | CBGS |
| 14 | days after treatment | | | | | | |
| 8 | lbs/acre application rate | 10 | 10 | 10 | 10 | 10 | 10 |
| 2 | " | 10 | 10 | 10 | 10 | 10 | 9 |
| 1 | " | 7* | 10* | 7* | 10* | 10* | 4* |
| 0.5 | " | 2 | 10 | 2 | 10 | 10 | 0 |
| 0.25 | " | 2 | 0 | 3 | 0 | 3 | 0 |
| 0.125 | " | 0 | 0 | 2 | 0 | 4 | 0 |

| | | Plant Species | | | | | |
|---|---|---|---|---|---|---|---|
| | | SUBT | SORG | WHT | RICE | COTN | VTLF |
| 14 | days after treatment | | | | | | |
| 8 | lbs/acre application rate | — | — | — | — | — | — |
| 2 | " | — | — | — | — | — | — |
| 1 | " | 10 | 2 | 10 | 4 | 3 | 10 |
| 0.5 | " | 10 | 0 | 5 | 2 | 2 | 4 |
| 0.25 | " | 10 | 0 | 3 | 2 | 0 | 3 |
| 0.125 | " | 4 | 0 | 2 | 2 | 0 | 2 |

| | | Plant Species | | | | | | |
|---|---|---|---|---|---|---|---|---|
| | | QKGS | CORN | PTBN | ALFA | OAT | SPGT | CTGS |
| 14 | days after treatment | | | | | | | |
| 8 | lbs/acre application rate | — | — | — | — | — | — | — |
| 2 | " | — | — | — | — | — | — | — |
| 1 | " | 10 | 2 | 10 | 10 | 4 | 4 | 3 |
| 0.5 | " | 10 | 2 | 4 | 7 | 3 | 0 | 4 |
| 0.25 | " | 10 | 0 | 2 | 2 | 3 | 0 | 0 |
| 0.125 | " | 5 | 0 | 2 | 0 | 0 | 0 | 0 |

*Average of two tests.

I claim:

1. A compound of the formula

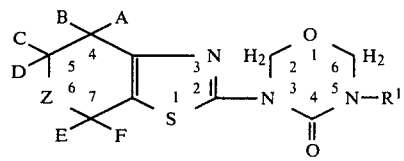

wherein $R^1$ is seleced from the group consisting of hydrogen and alkyl; Z is $-CHR^2-$; $R^2$ and $R^3$ are selected from the group consisting of hydrogen and alkyl; A, C and E are each independently selected from the group consisting of C1-C10 alkyl and hydrogen; B,D and F are each independently selected from the group consisting of C1-C10 alkyl, C3-C10 alkenyl, C4-C10 alkynyl, cycloalkyl, alkoxy, alkylthio, amino, cyano and hydrogen.

2. The compound of claim 1 which is, 3-(5,5,7,7-tetramethyl-4,5,6,7-tetrahydrobenzothiazol-2-yl)-5-methyltetrahydro-1,3,5-oxadiazin-4-one.

3. The compound of claim 1 which is, 3-(5,5,7,7-tetramethyl-44,5,6,7-tetrahydrobenzothiazol-2-yl)-5ethyl-tetrahydro-1,3,5-oxadiazin-4-one.

4. The compound of claim 1 which is, 3-(5,5,7,7-tetramethyl-4,5,6,7-tetrahydrobenzothiazol-2yl)-5-(1-methylethyl)tetrahydro-1,3,5-oxadiazin-4-one.

5. The compound of claim 1 which is, 3-(5,5,7,7-tetramethyl-4,5,6,7-tetrahydrobenzothiazol-2-yl)-5-hexyl-tetrahydro-1,3,5-oxadiazin-4-one.

6. The compound of claim 1 which is, 3-(5,5,7,7-tetramethyl-4,5,6,7-tetrahydrobenzothiazol-2-yl)tetrahydro-1,3,5-oxadiazin-4-one.

7. The compound of claim 1 which is, 3-(5,5,7-trimethyl-4,5,6,7-tetrahydrobenzothiazol-2-yl)-5-methyltetrahydro-1,3,5-oxadiazin-4-one.

8. A herbicidal composition comprising an inert carrier and, as an essential active ingredient, in a quantity toxic to weeds, a compound of claim 1.

9. A method of controlling weeds which comprises contacting said weeds with a herbicidal composition comprising an inert carrier and, as the essential active ingredient, in a quantity toxic to weeds, a compound of claim 1.

* * * * *